US011524032B2

(12) United States Patent
Burr et al.

(10) Patent No.: US 11,524,032 B2
(45) Date of Patent: Dec. 13, 2022

(54) TREATMENT OF MYOPIC PROGRESSION

(71) Applicant: University of Utah Research Foundation, Salt Lake City, UT (US)

(72) Inventors: Randon Michael Burr, Salt Lake City, UT (US); Balamurali K. Ambati, Sandy, UT (US); Sarah A. Molokhia, Sandy, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 16/960,077

(22) PCT Filed: Jan. 7, 2019

(86) PCT No.: PCT/US2019/012501
§ 371 (c)(1),
(2) Date: Jul. 4, 2020

(87) PCT Pub. No.: WO2019/136358
PCT Pub. Date: Jul. 11, 2019

(65) Prior Publication Data
US 2021/0060059 A1  Mar. 4, 2021

Related U.S. Application Data

(60) Provisional application No. 62/614,230, filed on Jan. 5, 2018.

(51) Int. Cl.
*A61K 33/34* (2006.01)
*A61P 27/10* (2006.01)
*A61K 9/00* (2006.01)
*A61K 45/06* (2006.01)

(52) U.S. Cl.
CPC ............ *A61K 33/34* (2013.01); *A61K 9/0051* (2013.01); *A61K 45/06* (2013.01); *A61P 27/10* (2018.01)

(58) Field of Classification Search
CPC .... A61K 33/34; A61K 9/0051; A61K 9/0048; A61K 45/06; A61P 27/10
See application file for complete search history.

(56) References Cited

U.S. PATENT DOCUMENTS

| | | |
|---|---|---|
| 3,416,530 A | 12/1968 | Ness. |
| 5,075,105 A | 12/1991 | Avetisov et al. |
| 6,455,061 B2 * | 9/2002 | Richardson .......... A61K 9/0034 424/422 |
| 2003/0175259 A1 * | 9/2003 | Karageozian .......... A61P 27/10 424/94.1 |
| 2006/0134226 A1 | 6/2006 | Leonard |
| 2006/0276777 A1 * | 12/2006 | Coroneo ................ A61K 31/47 606/5 |
| 2014/0343480 A1 * | 11/2014 | Kamaev ............... A61K 31/519 514/249 |
| 2015/0366854 A1 | 12/2015 | Ostrow et al. |
| 2016/0338947 A1 | 11/2016 | Leahy et al. |
| 2019/0083529 A1 | 3/2019 | Ambati et al. |

FOREIGN PATENT DOCUMENTS

| | | | |
|---|---|---|---|
| EP | 3103446 A2 | 12/2016 | |
| WO | WO-02083873 A2 * | 10/2002 | ............... C12N 9/00 |
| WO | WO 2008005705 A2 | 1/2008 | |
| WO | WO 2017/155580 A1 | 9/2017 | |
| WO | WO 2019104191 A1 | 5/2019 | |

OTHER PUBLICATIONS

Wollensak et al., Collagen crosslinking of human and porcine sclera, Mar. 2004, Journal of Cataract & Refractive Surgery, vol. 30 iss. 3, pp. 689-695. (Year: 2004).*
Dudakova et al., Is copper imbalance an environmental factor influencing keratoconusdevelopment?, May 2015, Medical Hypotheses, vol. 84 iss. 5, pp. 518-524. (Year: 2015).*
Wikipedia.; (Orthokeratology) Version: Sep. 18, 2017, Retrieved Apr. 1, 2019; (http://en.wikipedia.org/w/index.php?title=Orthokeratology&oldid=801266165); p. 1, para 1; 5 Pages.
PCT Application No. PCT/US19/12501 Filing date Jan. 7, 2019; Randon Michael Burr; International Search Report dated Apr. 30, 2019; 12 Pages.
Makris E.A.; "A copper sulfate and hydroxy lysine treatment regimen for enhancing collagen crosslinking and biomechanical properties in engineered neocartilage;" The FASEB Journal; Jun. 2013; vol. 27: pp. 2421-2430.

* cited by examiner

*Primary Examiner* — Ali Soroush
(74) *Attorney, Agent, or Firm* — Thorpe North & Western, LLP; David W. Osborne

(57) ABSTRACT

An ophthalmic composition or dosage form can include a therapeutically effective amount of a copper-containing agent that is sufficient to increase corneal lysyl oxidase activity in an eye of a subject in an amount sufficient to treat myopic progression and a pharmaceutically acceptable carrier. The composition or dosage form can be used to treat or prevent progression of myopia by administering a therapeutically effective amount of the composition to an eye of a subject during a treatment period.

19 Claims, 10 Drawing Sheets

TREATMENT OF MYOPIC PROGRESSION

PRIORITY DATA

This application claims the benefit of U.S. Provisional Patent Application Ser. No. 62/614,230, filed on Jan. 5, 2018, which is incorporated herein by reference.

BACKGROUND

Myopia is a common cause of vision loss. The underlying defect of myopia is a slightly elongated eyeball that causes the ocular lens to focus light from far objects slightly in front of the retina. Uncorrected myopia is one of the leading causes of impaired distance vision in the world. In severe cases, the elongation of the eyeball can stretch and thin some of the inner parts of the eye, which can increase the risk of retinal detachment, cataracts, glaucoma, blindness, etc. Further, prevalence of myopia is increasing and is expected to affect half of the global population by 2050.

Figure 1A:
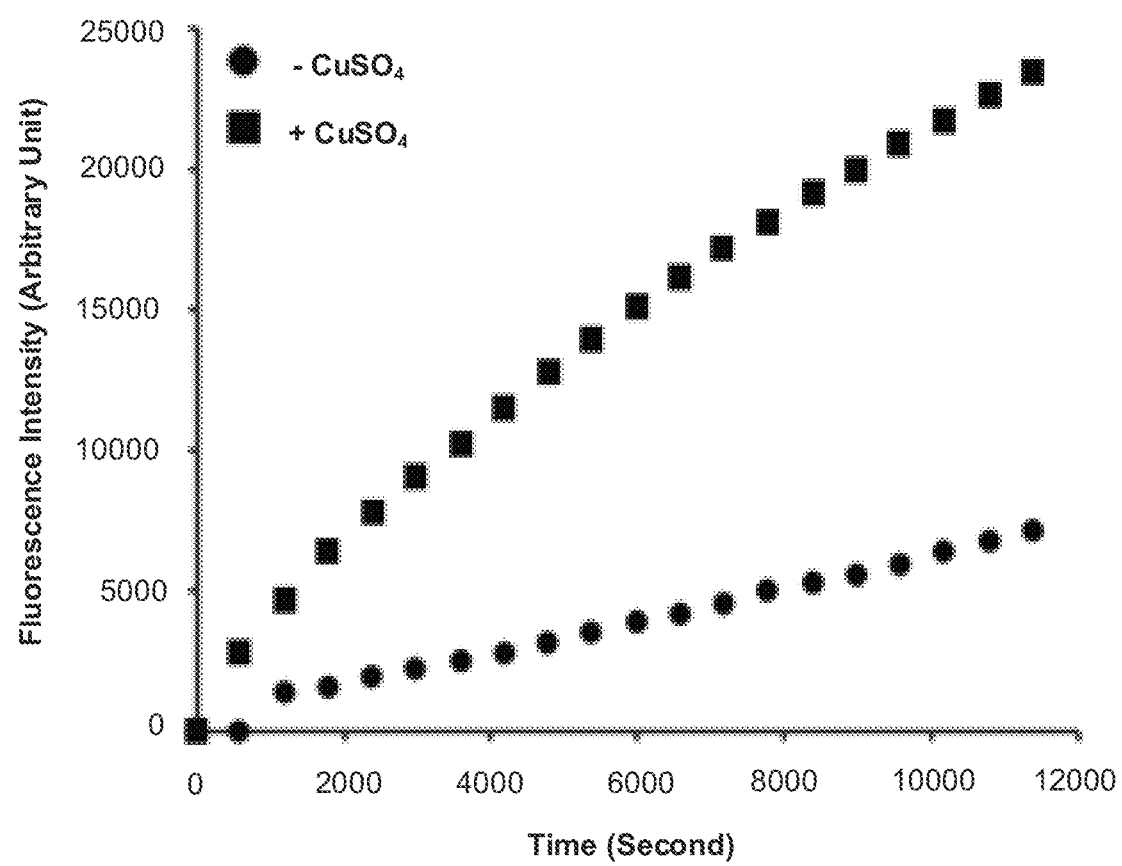
FIG. 1A is a graph showing increased lysyl oxidase activity in corneal fibroblast cells in response to Cu treatment.

These drawings are provided to illustrate various aspects of the invention and are not intended to be limiting of the scope in terms of dimensions, materials, configurations, arrangements or proportions unless otherwise limited by the claims.

DESCRIPTION OF EMBODIMENTS

Although the following detailed description contains many specifics for the purpose of illustration, a person of ordinary skill in the art will appreciate that many variations and alterations to the following details can be made and are considered to be included herein. Accordingly, the following embodiments are set forth without any loss of generality to, and without imposing limitations upon, any claims set forth. It is also to be understood that the terminology used herein is for the purpose of describing particular embodiments only, and is not intended to be limiting. Unless defined otherwise, all technical and scientific terms used herein have the same meaning as commonly understood by one of ordinary skill in the art to which this disclosure belongs.

As used in this written description, the singular forms "a," "an" and "the" include plural referents unless the context clearly dictates otherwise. Thus, for example, reference to "a cell" includes a plurality of such cells.

In this disclosure, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open ended term, like "comprising" or "including," in the written description it is understood that direct support should be afforded also to "consisting essentially of" language as well as "consisting of" language as if stated explicitly and vice versa.

The terms "first," "second," "third," "fourth," and the like in the description and in the claims, if any, are used for distinguishing between similar elements and not necessarily for describing a particular sequential or chronological order. It is to be understood that any terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

The term "coupled," as used herein, is defined as directly or indirectly connected in a biological, chemical, mechanical, electrical or nonelectrical manner. "Directly coupled" structures or elements are in contact with one another and are attached. Objects described herein as being "adjacent to" each other may be in physical contact with each other, in close proximity to each other, or in the same general region or area as each other, as appropriate for the context in which the phrase is used. Occurrences of the phrase "in one embodiment," or "in one aspect," herein do not necessarily all refer to the same embodiment or aspect.

As used herein, the terms "therapeutic agent," "active agent," and the like can be used interchangeably and refer to an agent that can have a beneficial or positive effect on a subject when administered to the subject in an appropriate or effective amount. In one aspect, the therapeutic or active agent can be a copper-containing material or compound.

As used herein, an "effective amount" of an agent is an amount sufficient to accomplish a specified task or function desired of the agent. A "therapeutically effective amount" of a composition, drug, or agent refers to a non-toxic, but sufficient amount of the composition, drug, or agent, to achieve therapeutic results in treating or preventing a condition for which the composition, drug, or agent is known to be effective. It is understood that various biological factors may affect the ability of a substance to perform its intended task. Therefore, an "effective amount" or a "therapeutically effective amount" may be dependent in some instances on such biological factors. Further, while the achievement of therapeutic effects may be measured by a physician, veterinarian, or other qualified medical personnel using evaluations known in the art, it is recognized that individual variation and response to treatments may make the achievement of therapeutic effects a somewhat subjective decision. The determination of an effective amount or therapeutically effective amount is well within the ordinary skill in the art of pharmaceutical sciences and medicine.

As used herein, a "dosing regimen" or "regimen" such as "treatment dosing regimen," or a "prophylactic dosing regimen" refers to how, when, how much, and for how long a dose of an active agent or composition can or should be administered to a subject in order to achieve an intended treatment or effect.

As used herein, the terms "treat," "treatment," or "treating" refers to administration of a therapeutic agent to subjects who are either asymptomatic or symptomatic. In other words, "treat," "treatment," or "treating" can be to reduce, ameliorate or eliminate symptoms associated with a condition present in a subject, or can be prophylactic, (i.e. to prevent or reduce the occurrence of the symptoms in a subject). Such prophylactic treatment can also be referred to as prevention of the condition.

As used herein, the terms "formulation" and "composition" are used interchangeably and refer to a mixture of two or more compounds, elements, or molecules. In some aspects the terms "formulation" and "composition" may be used to refer to a mixture of one or more active agents with a carrier or other excipients. Compositions can take nearly any physical state, including solid, liquid (e.g. solution), or gas. Furthermore, the term "dosage form" can include one or more formulation(s) or composition(s) provided in a format for administration to a subject. For example, an injectable dosage form would be a formulation or composition prepared in a manner that is suitable for administration via injection.

As used herein, a "subject" refers to an animal. In one aspect the animal may be a mammal. In another aspect, the mammal may be a human.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, comparative terms such as "increasing," "increased," "decreasing," "decreased," "better," "worse," "higher," "lower," "enhancing," "enhanced," "maximizing," "maximized," "minimizing," "minimized," and the like refer to a property, result, or effect of a device, composition, formula, component, treatment, regimen, method, or activity that is measurably different from a property, result, or effect of other devices, compositions, formulas, components, treatments, regimens, methods, or activities. Furthermore, comparative terms can refer to a different biological state, presence, absence, activity level, or operation that is measurably different than an endogenous biological state, presence, absence, activity level, or operation. Comparative terms can be used to indicate differences in a surrounding or adjacent area, for example, regions of tissue. Comparative terms can also be used to indicate differences in chemical or biological structure or activity (e.g. therapeutic activity or effectiveness). Additionally, comparative terms can be used to indicate differences in biologic or physiologic result, activity, or status as compared to a previous, or other biologic or physiologic result, activity, or status. For example, an increase or decrease in lysyl oxidase activity can be identified by comparing an amount of lysyl oxidase at a first time point, compared to an amount at a second time point. In the instance that a composition or treatment has been applied, such increase or decrease can be attributed to such composition or treatment. More specifically, an increase in lysyl oxidase by an applied composition or treatment can be determined or otherwise quantified by either measuring an amount of lysyl oxidase prior to application of the composition or treatment, and then again after application of the composition or treatment. In some cases, comparison may be made simply between the points in time (e.g. endogenous state versus treated state). In other cases, the comparison can be made between the results achieved by two different applied formulations or treatment (e.g. formulations having different amounts of an active agent, etc.).

As used herein, the term "about" is used to provide flexibility to a numerical range endpoint by providing that a given value may be "a little above" or "a little below" the endpoint. Unless otherwise stated, use of the term "about" in accordance with a specific number or numerical range should also be understood to provide support for such numerical terms or range without the term "about". For example, for the sake of convenience and brevity, a numerical range of "about 50 micrograms to about 80 micrograms" should also be understood to provide support for the range of "50 micrograms to 80 micrograms." Furthermore, it is to be understood that in this specification support for actual numerical values is provided even when the term "about" is used therewith. For example, the recitation of "about" 30 should be construed as not only providing support for values a little above and a little below 30, but also for the actual numerical value of 30 as well.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

This same principle applies to ranges reciting only one numerical value as a minimum or a maximum. Furthermore, such an interpretation should apply regardless of the breadth of the range or the characteristics being described.

Reference throughout this specification to "an example" means that a particular feature, structure, or characteristic described in connection with the example is included in at least one embodiment. Thus, appearances of the phrases "in an example" in various places throughout this specification are not necessarily all referring to the same embodiment.

Example Embodiments

An initial overview of invention embodiments is provided below and specific embodiments are then described in further detail. This initial summary is intended to aid readers in understanding the technological concepts more quickly, but is not intended to identify key or essential features thereof, nor is it intended to limit the scope of the claimed subject matter.

Myopia can be a severely debilitating ocular condition. The underlying defect of myopia is a slightly elongated eyeball that causes the ocular lens to focus light from far objects slightly in front of the retina. Thus, myopia is often referred to as short-sightedness or near-sightedness. In severe cases, this elongation of the eyeball can stretch and thin some of the inner parts of the eye, which can increase the risk of retinal detachment, cataracts, glaucoma, blindness, etc. As such, myopia can be much more severe than mere short-sightedness.

Various causes of myopia have been suggested and studied, such as genetic predisposition, prolonged book-work or screen-time, inadequate exposure to bright light, etc. Regardless of the underlying cause of myopia in any given case, which may be one or more of those listed above, the elongated eyeball associated with myopia can be debilitating for all inflicted with this condition. Because the eye grows throughout childhood, myopia generally develops in school-age children and adolescents and can remain with these individuals throughout their lives. Therefore, improved treatments for individuals, such school-age children and adolescents, can improve the quality of life for these individuals both during their youth and throughout their lives.

Accordingly, the present disclosure is directed to compositions and methods of treating and/or preventing progression of myopia in an individual, such as a school-age child, adolescent, or young adult. In some examples, treating and/or preventing progression of myopia can include administration of a therapeutically effective amount of an ophthalmic composition or dosage form to a subject in need thereof.

In one example, an ophthalmic composition or dosage form is described herein. The ophthalmic composition or dosage form can include an amount of a copper-containing agent, or other cross-linking agent, that is sufficient to increase lysyl oxidase activity in an eye of a subject or otherwise increase cross-linking in the cornea of the subject to a degree that slows or arrests myopic progression. The composition or dosage form can further include a pharmaceutically acceptable carrier. In some examples, the dosage form can be an ophthalmic composition formulated as a topical eye drop and carried in a container adapted to dispense the composition in a drop-wise manner at a drop volume of from about 5 µl to about 100 µl. In some examples, the ophthalmic composition can be a sustained release composition that is formulated to release the copper-containing agent over a prolonged period of time. In another embodiment, a method is described for using such a composition or dosage form. The method can include administering a therapeutically effective amount of a composition or dosage form, as described herein, during a treatment period.

In some cases, myopia can be characterized by decreased corneal stiffness. However, as will be more apparent by the various embodiments and examples provided herein, the compositions, dosage forms, and methods described in the current disclosure can increase corneal lysl oxidase activity in an eye of a subject, can increase collagen crosslinks (e.g. LNL, HLNL, DHLNL, etc.) in the cornea, can increase corneal tissue strength in an eye of a subject, and can provide a number of other benefits described herein that can help increase corneal stiffness and flatten out a myopic cornea to treat or prevent progression of myopia in an individual.

In further detail, copper is a co-factor for lysyl oxidase (LOX), an enzyme that forms various types of collagen cross-links. As such, copper supplementation via a copper-containing salt, compound, chelate, the like, or a combination thereof can be used to increase collagen bonds. Such supplementation can improve the biomechanical properties of myopic corneas by increasing lysyl oxidase activity. Because low corneal stiffness and an elongated cornea can be associated with myopia and copper supplementation can improve biomechanical properties of the cornea and induce corneal flattening, topical or other suitable copper treatment can provide a non-invasive and relatively cost-effective tool for treating and/or preventing the progression of myopia.

Accordingly, an ophthalmic composition or dosage form is described herein that can include an amount of a copper-containing agent that is sufficient to increase lysyl oxidase activity in an eye of a subject or otherwise increase corneal cross-linking in an amount sufficient to treat or prevent myopic progression in the subject. A variety of copper-containing agents can be used, such as a copper-containing salt, compound, chelate, or the like. Non-limiting examples of copper salts can include copper sulfates, copper carbonates, copper acetates, copper chlorides, copper bromides, copper fluorides, copper nitrates, copper hydroxides, copper iodides, copper perchlorates, copper molybdates, copper thiocyanates, copper tartrates, copper tetrafluoroborates, copper selenides, copper pyrophosphates, hydrates thereof, the like, or combination thereof. Other suitable copper carriers can include GHK-copper, tetra-amine copper sulfate, copper-histidine, copper-glycinate, copper-gluconate, hydrates thereof, the like, or combinations thereof. In some specific examples, the copper-containing agent can be a copper-containing salt. In some examples, the copper salt can be copper (II) sulfate, or copper (II) sulfate pentahydrate.

Thus, the copper-containing agent can be any suitable copper-containing agent that can provide a therapeutically effective amount of copper to an eye of the subject. The therapeutically effective amount can be sufficient to increase corneal lysyl oxidase activity in the eye to a degree that slows or arrests myopic progression, for example by increasing collagen cross-linking as compared to collagen cross-linking prior to treatment. This can also increase the biomechanical strength of the cornea as compared to the biomechanical strength prior to treatment. Further, this can decrease the diopter of the cornea in the treated eye as compared to the diopter prior to treatment.

A therapeutically effective amount of a copper-containing agent can be based upon the amount of copper carried by the copper-containing agent. In some examples, the copper-containing agent can provide a composition having copper levels less than about 0.1 mg/ml, about 0.05 mg/ml, about 0.02 mg/ml, about 0.005 mg/ml, or about 0.002 mg/ml, but that are still effective at increasing lysyl oxidase activity to a degree that slows or arrests myopic progression. It can be important to keep the copper level sufficiently low to avoid copper-induced toxicity, while maintaining a sufficient amount of bioavailable copper to increase lysyl oxidase activity.

Thus, the therapeutically effective amount of the copper-containing agent can be determined based on the type of delivery vehicle, the type of copper-containing agent, the desired delivery duration, etc. For example, depending on the how the composition is formulated, the composition can include an amount of copper from about 0.00001 mg/ml or about 0.00005 mg/ml to about 5 mg/ml or about 50 mg/ml. In other examples, the composition can include an amount of copper from about 0.00006 mg/ml to about 0.07 mg/ml, from about 0.0006 mg/ml to about 0.007 mg/ml, from about 0.0005 mg/ml to about 0.03 mg/ml, from about 0.01 mg/ml to about 5 mg/ml, or from about 0.001 to about 0.005 mg/ml. In some additional examples, the composition can include an amount of copper from about 0.0001 mg/ml to about 0.05 mg/ml, about 0.00025 mg/ml to about 0.015, about 0.0005 mg/ml to about 0.00075 mg/ml, or about 0.0008 mg/ml to about 0.0011 mg/ml. Thus, in some examples, the therapeutically effective amount can be defined as the amount of copper included in the composition. For example, an amount of 0.0025 mg/ml of copper (II) sulfate pentahydrate provides the composition with a copper content of about 0.000636 mg/ml copper. This is because the atomic weight of copper (II) sulfate pentahydrate is about 249.677 g/mol, but only about 63.5 g/mol or about 25% of the agent is copper itself. As an alternative example, an amount of 0.0018 mg/ml of copper (II) acetate, anhydrous, provides the composition with a copper content of about 0.00063 mg/ml. Thus, the therapeutically effective amount can be determined based on the copper content provided by the copper-containing agent rather than the amount of copper-containing agent itself.

Alternatively, the therapeutically effective amount can be defined as a wt % of the copper-containing agent in the composition. Again, depending on how the composition is formulated, the therapeutically effective amount of the copper-containing agent can be an amount from about 0.00001 wt % or about 0.0001 wt % to about 5 wt %, 10 wt %, or 15 wt %. In some examples, the therapeutically effective amount of the copper-containing agent can be from about 0.05 wt % to about 15 wt %, from about 0.01 wt % to about 10 wt %, or from about 0.005 wt % to about 5 wt %. In other examples, the therapeutically effective amount of the copper-containing agent can be an amount from about 0.00001 wt % to about 0.0001 wt %, from about 0.0001 wt % to about 0.0005 wt %, from about 0.0001 wt % to about 0.0002 wt %, from about 0.0002 wt % to about 0.0003 wt %, or from about 0.0003 wt % to about 0.0004 wt %. In yet other examples, the therapeutically effective amount of the copper-containing agent can be an amount from about 0.001 wt % to about 0.01 wt % or about 0.003 wt % to about 0.008 wt %. In yet other examples, the therapeutically effective amount of the copper-containing agent can be an amount from about 0.01 wt % to about 0.1 wt %, or from about 0.03 wt % to about 0.08 wt %. It is noted that these weight percentages are calculated based on copper (II) sulfate, anhydrous. Thus, where an alternative copper-containing agent is employed, the weight percentages can be converted accordingly.

However, a particular amount of copper-containing agent in the composition does not necessarily mean that all of the copper content will be bioavailable upon administration or will become bioavailable at the same rate. The bioavailability of the copper can vary to some extent from one copper-containing component to another. Additionally, the bioavailability of the copper can be affected by pH, viscosity, solubility, and other compositional factors. Thus, the therapeutically effective amount of copper-containing agent can also be adjusted based on the bioavailability of copper with respect to a particular copper carrier, pH, formulation, or the like. Further, the release rate of the copper content from a particular dosage form can be adjusted based on the particular copper-containing agent employed in the dosage form. For example, in some cases a less soluble copper-containing agent (e.g. copper fluoride, copper hydroxide, copper carbonate, for example) can be used to prolong the release of the copper-containing agent from the composition. In some further examples, the release rate can additionally or alternatively be controlled via a particular pharmaceutical carrier or formulation type.

In some cases, the copper-containing agent can also be administered with a therapeutically effective amount of a second active or therapeutic agent. In some examples, the second active agent can be an additional crosslinking agent. In some examples, the second active agent can provide additional mechanisms of action working in concert with the crosslinking induced by the copper containing agent and/or other crosslinking agent. For example, second active agents can reduce axial elongation, reduce accommodation (i.e. the process by which the eye changes optical power to maintain a clear focus on an image as its distance varies), the like, or a combination thereof. Such additional agents can include riboflavin, rose bengal, hydroxylysine, a calcium-containing agent, a magnesium-containing agent, a silver-containing agent, an aluminum-containing agent, a zinc-containing agent, iron-containing agent, acai extract, decorin, biglycan, keratocan, lumican, mimican, fibromodulin, type VI collagen, type X collagen, type XII collagen, type XIV collagen, atropine, homatropine, cyclopentolate, pirenzepine, 7-methylxanthanine, the like, or combinations thereof. In some examples, the additional or second active agent can include atropine, homatropine, cyclopentolate, pirenzepine, 7-methylxanthanine, the like, or a combination thereof. In some specific examples, the second active agent can include atropine. In some additional examples, the second active agent can include homatropine. In still additional examples, the second active agent can include cyclopentolate. In further examples, the second active agent can include pirenzepine. In still further examples, the second active agent can include 7-methylxanthanine. The second active agent can generally be present in an amount from about 0.001 wt % to about 0.1 wt %. In other examples, the second active agent can be present in an amount from about 0.005 wt % to about 0.05 wt %, or from about 0.007 wt % to about 0.02 wt %.

Additionally, in some examples, a plurality of different copper-containing agents can be administered concurrently, with or without a second active or therapeutic agent. It is also noted that in some examples one or more alternative cross-linking agents can be administered instead of a copper-containing agent. For example, in some cases an alternative cross-linking agent can be or include any divalent or multivalent ion or compound that is suitable to induce or facilitate cross-linking in the cornea. In some examples, the cross-linking agent can be or include a metal ion, such as an alkaline earth metal, a transition metal, a post-transition metal, the like, or combinations thereof, for example. In some examples, the cross-linking agent can be or include a cation. In some specific examples, the cross-linking agent can be or include a divalent metal ion, such as magnesium, iron, zinc, or the like.

The copper-containing agent can be provided in a pharmaceutically acceptable carrier. The pharmaceutically acceptable carrier can be formulated in a variety of ways to deliver the copper-containing agent. Non-limiting examples can include solutions, suspensions, emulsions, gels, hydrogels, thermo-responsive gels, formulation for subconjunctival injection, formulation for sub-tenon's injection, depots, films, sustained-delivery matrixes, contact lenses, pledgets, punctal plugs, gellating suspensions, the like, or a combination thereof. In some examples, the composition can be formulated for passive delivery to the eye. In other examples, the composition can be formulated for active delivery to the eye, such as iontophoresis, electroporation, sonoporation, etc. In one specific example, the formulation can be an ophthalmic drop. In some examples, the composition can be formulated as a copper-eluting contact lens, such as a soft lens, a toric lens, a hard lens, a scleral lens, the like, or combination thereof. The contact lens can be a daily disposable lens or extended use lens (e.g. from 2 days-use to 2 week-use lenses or longer). In some examples, the composition can be formulated as a sustained-delivery matrix for placement in contact with an ocular surface, such as in a cul-de-sac, conjunctiva, tenon's capsule or sub-tenon's space, etc. In some examples, the composition can be formulated as a biodegradable device, such as a lens, film, capsule, punctal plug, the like, or a combination thereof. The biodegradable device can be configured to biodegrade at a rate of from about 1 week to about 6 months, or from about 2 weeks to about 4 months, or from about 1 month to about 2 months.

Depending on how the composition is formulated, the pharmaceutically acceptable carrier can include a variety of excipients. For example, a pharmaceutically acceptable carrier can include one or more of a solubilizing agent, a tonicity agent, a pH adjuster, a thickener or gelling agent, a polymer or polymeric matrix, a preservative, water, the like, and combinations thereof.

Non-limiting examples of solubilizing agents can include phosphate-buffered saline (PBS), Dulbecco's PBS, Alsever's solution, Tris-buffered saline (TBS), water, balanced salt solutions (BSS), such as Hank's BSS, Earle's BSS, Grey's BSS, Puck's BSS, Simm's BSS, Tyrode's BSS, BSS Plus, Ringer's lactate solution, normal saline (i.e. 0.9% saline), ½ normal saline, the like, or combinations thereof. Solubilizing agents can be present in the pharmaceutically acceptable carrier in various amounts depending on the particular formulation, method of treatment, etc.

Non-limiting examples of tonicity agents can include the solubilizing agents previously listed, as well as sodium chloride, potassium chloride, calcium chloride, magnesium chloride, mannitol, sorbitol, dextrose, glycerin, propylene glycol, ethanol, trehalose, the like, or combinations thereof. The tonicity agent can be used to provide an appropriate tonicity of the formulation. In one aspect, the tonicity of the formulation is from about 200 to about 600 milliosmoles/liter (mOsm/L). In another aspect, the tonicity of the formulation can be from about 250 mOsm/L to about 350 mOsm/L. In another aspect, the tonicity of the formulation can be from about 350 mOsm/L to about 450 mOsm/L. In another aspect, the tonicity of the formulation can be from about 450 mOsm/L to about 550 mOsm/L. In still another aspect, the tonicity of the formulation can be from about 400 mOsm/L to about 600 mOsm/L, from about 400 mOsm/L to about 500 mOsm/L, or from about 500 mOsm/L to about 600 mOsm/L. Tonicity agents can be present in the pharmaceutically acceptable carrier in various amounts depending on the particular formulation, method of treatment, etc.

Non-limiting examples of pH adjusters can include a number of acids, bases, and combinations thereof, such as hydrochloric acid, phosphoric acid, citric acid, sodium hydroxide, potassium hydroxide, calcium hydroxide, and the like. The pH adjusters can be used to provide an appropriate pH for the formulation. Where applicable, in one aspect, the pH can be from about 5.5 to about 8.5. In one aspect, the pH can be from about 5.8 to about 7.8. In another aspect, the pH can be from about 6.5 to about 7.8. In yet other examples, the pH can be from about 7.0 to about 7.6. pH adjusters can be present in the pharmaceutically acceptable carrier in various amounts depending on the particular formulation, method of treatment, etc.

Non-limiting examples of thickeners or gelling agents can include glycerol, propylene glycol, polyethylene glycol, polyvinyl alcohol, cellulose derivatives (such as methyl cellulose, carboxymethyl cellulose, hydroxypropyl cellulose, and the like) ethylvinyl alcohol, hyaluronic acid, the like, or combinations thereof. Thickeners or gelling agents can be present in the pharmaceutically acceptable carrier in various amounts depending on the particular formulation, method of treatment, etc.

Non-limiting examples of polymers that can be used to prepare a polymer matrix for a film, contact lens or the like, can include biodegradable or non-biodegradable polymers. Non-limiting examples of polymers or polymer combinations can include poly(methylmethacrylate), polyorthoesters, hydroxyethylmethacrylate, polysiloxanes, poly(lactic-co-glycolic acid) (different ratios of lactic to glycolide content and end groups such as acid or ester termination), polyvinyl alcohol, polyvinyl acetate, ethylene vinyl acetate, polyethylene glycol, polylactic acid, polyglycolic acid, hydroxypropyl methylcellulose, hydroxypropylcellulose, carboxymethylcellulose, croscarmellose, polycaprolactone, hyaluronic acid, albumin, sodium chloride block copolymers thereof, salts thereof, the like, or combinations thereof. Specific copolymers such as polylactic-polyglycolic acid block copolymers (PLGA), polyglycolic acid-polyvinyl alcohol block copolymers (PGA/PVA), hydroxypropylmethylcellulose (HPMC), polycaprolactone-polyethylene glycol block copolymers, croscarmellose, and the like can be particularly effective for biodegradable matrixes, where desirable.

In some examples, the composition can include thermo-responsive polymers. Non-limiting examples of thermo-responsive polymers can include poly(N-isopropyl acrylamide), poly [2-(dimethylamino)ethylmethacrylate], hydroxypropylcellulose, poly(vinyl caprolactame), polyvinyl methyl ether, polyethylene oxide, polyhydroxyethylmethacrylate, ABCBA-type pentablock polymers, chitosan, the like, or combinations thereof. Such thermo-responsive polymers can bind or can be functionalized to bind a particular copper-containing agent within a range of temperatures and release the copper-containing agent upon changing the temperature of the surrounding environment, such as placing the composition in contact with the eye, applying a heat source to the eye after administration of the composition, or the like.

Non-limiting examples of preservatives can include benzalkonium chloride (BAK), cetrimonium, sodium perborate, ethylenediaminetetraaceticacid (EDTA) and its various salt forms, chlorobutanol, and the like. Preservatives can be present in the pharmaceutically acceptable carrier in various amounts depending on the particular formulation, method of treatment, etc.

In one specific example, the pharmaceutically acceptable carrier can be formulated as an ophthalmic drop and can include PBS, BSS, or other suitable solubility or tonicity agent. In another specific example, the pharmaceutically acceptable carrier can be formulated as an ophthalmic drop and can include artificial tears (e.g. Refresh Tears®, Genteal®, Oasis Tears®, or the like). In some additional examples, the pharmaceutically acceptable carrier can be formulated as a thin film, ointment, gellating suspension, punctal plug, or contact lens.

Regardless of how the ophthalmic composition is formulated, the ophthalmic composition can be used as an ophthalmic dosage form to administer a therapeutically effective dose of the copper-containing agent. In some examples, the ophthalmic dosage form can provide from about 0.0005 µg to about 0.5 µg of copper per administration event. In yet other examples, the ophthalmic dosage form can provide from about 0.006 µg to about 0.06 µg, about 0.01 µg to about 0.03 µg, or about 0.016 µg to about 0.044 µg of copper per administration event. In other examples, the ophthalmic dosage form can provide from about 0.0005 µg to about 5 µg of copper per day, on average. In yet other examples, the ophthalmic dosage form can provide from about 0.001 µg to about 2 µg, about 0.006 µg to about 0.24 µg, about 0.01 µg to about 0.12 µg, or about 0.016 µg to about 0.18 µg of copper per day, on average. It is noted that not all of the copper that is provided by the dosage form necessarily becomes bioavailable, but in some examples it can.

In some examples, the ophthalmic dosage form can be used in an effective dosage regimen to provide a therapeutically effective amount of the copper-containing agent. In some examples, the ophthalmic dosage form can be formulated for daily administration of the copper-containing agent. Where this is the case, the effective dosage regimen can include administering the ophthalmic dosage form once per day, twice per day, three times per day, four times per day, or more.

In yet other examples, the ophthalmic dosage form can be formulated to biodegrade to otherwise provide controlled or sustained release of the copper-containing agent over a predetermined period of time. In yet other examples, the ophthalmic dosage form can be formulated to release the copper-containing agent from a non-biodegradable matrix in a controlled or sustained manner. In examples such as these, the dosage form can be formulated to release the copper-containing agent over a period of hours, days, or weeks, as desired. In some specific examples, the dosage form can be formulated to deliver from about 0.005 mcg of copper to about 250 mcg of copper per week. In yet other examples, the dosage form can be formulated to deliver from about 0.008 mcg to about 200 mcg per week, about 0.01 mcg to about 150 mcg per week, or about 0.1 mcg to about 100 mcg per week. Further, the dosage form can typically be formulated to have zero-order drug release kinetics, although this is not required.

In some examples, the dosage form can be held in or stored in a container as a pre-mixed composition that is ready to administer without further dilution or preparation. In some embodiments, a single container can hold a volume or amount of the composition that is adequate for a single dose, but less than an amount that is adequate for a plurality of doses. In yet other examples, a single container can hold a volume or amount of the composition that is adequate for multiple doses.

A number of suitable containers can be used. In one aspect, the container can be an amber-colored container. In some examples, the container can be made of glass, polypropylene, polyethylene, polycarbonate, polyvinylchloride, the like, or a combination thereof. In some examples, the container can have a volume of from about 0.5 ml to about 50 ml. In another aspect, the container can have a volume of from about 1 ml to about 30 ml, about 5 ml to about 20 ml, or about 3 ml to about 15 ml. In one aspect, the container can hold a single dose of the therapeutic composition or dosage form. In another aspect, the container can hold a plurality of doses of the therapeutic composition or dosage form. In some examples, the container can be a vial, a bottle, a blister pack, a sachet, or the like.

In some examples, about 0.005 mg to about 1 mg of the copper-containing agent can be included in the container. In yet other examples, about 0.01 mg to about 0.5 mg of the copper-containing agent can be included in the container. In some examples, about 0.001 mg to about 0.5 mg of copper can be included in the container. In some examples, about 0.005 mg to about 0.2 mg of copper can be included in the container.

In some specific examples, the dosage form can be a topical ophthalmic dosage form that is formulated as an eye drop and carried in a container adapted to dispense the composition in a drop-wise manner at a drop volume of from about 5 µl to about 100 µl. Where the composition is formulated as an eye drop, in some examples, the container can include a fitted nozzle or tip from which the composition can be dispensed. As such, the container can typically be collapsible to dispense the composition. However, in some cases, after the composition is dispensed, air can be sucked back into the container, which can contaminate the composition. In some examples, the nozzle or tip can include a valve mechanism, filter, the like, or combination thereof to prevent or minimize introduction of bacteria and other contaminants into the container. Additionally, as previously discussed, the container can be adapted to dispense the ophthalmic composition in a drop-wise manner. For example, the container can be adapted to dispense the ophthalmic composition at a drop volume of from about 5 µl to about 50 µl, such as about 15 µl, about 20 µl, about 25 µl, about 30 µl, about 35 µl, about 40 µl, about 45 µl, or about 50 µl. In some specific examples, the drop volume can be from about 15 µl to about 40 µl, about 5 µl to about 30 µl about 20 µl to about 30 µl, about 25 µl to about 35 µl, or about 30 µl to about 40 µl.

Further included with dosage form can be an administration mechanism, such as a syringe, a dropper, or other mechanism. In additional embodiments, suitable packaging can be used to provide the composition, container, and instructions for the use thereof, and optionally an administration mechanism in a single integrated system.

The compositions or dosage forms described herein can also be employed in a method of treating and/or preventing progression of myopia. Such a method can include administering a therapeutically effective amount of the composition or dosage form to an eye of a subject during a treatment period.

In one example, the composition or dosage form can be administered at from 1 to 4 time points per day per eye in need thereof. In some examples, such as where the composition is an eye drop, the dosage amount of the composition at each time point can be from about 5 µl to about 100 µl about 5 µl to about 50 µl about 5 µl to about 30 µl, about 20 µl to about 30 µl, about 25 µl to about 35 µl, or about 30 µl to about 40 µl. The dosage form can generally provide from about 0.0005 µl to about 500 µl of copper per drop of the ophthalmic composition. In some additional examples, the dosage form can provide from about 0.0001 µl to about 5 µg, from about 0.001 µl to about 50 µl, or from about 0.005 µl to about 1 µg copper per drop of the ophthalmic composition.

In some further examples, the composition or dosage form can be administered multiple times per day, once per day, once every 2-5 days, once per week, once every two weeks, etc. In some cases, the composition can be formulated to have a sustained release profile of from about 2-5 days, about 1 week, about 2 weeks, or the like.

The treatment period can depend on a number of factors, such as the severity of the condition, the age of the subject at diagnosis, or the like. For example, in some cases, where the subject is a school-age child, adolescent, or young adult (e.g. from about age of 3 years to about age of 25 years, or from about age of 5 years to about age of 18 years from the date of birth), the subject can receive treatment for a period of from about 6 months to chronic treatment, or from about one year to about 5 years, or from about two years to about three years, or other suitable period of time until a desired outcome is achieved.

In some examples, the ophthalmic composition can be administered as an ophthalmic drop. In yet other examples, the ophthalmic composition can be administered as a subconjuntival injection. In other examples, the ophthalmic composition can be administered as a sub-tenon's injection. In yet other examples, the ophthalmic composition can be administered in the form of a topical film, topical gel, contact lens, punctal plug, or the like. In some examples, the topical film, topical gel, contact lens, punctal plug, or the like can be configured to biodegrade over time to provide controlled and sustained release of the copper-containing agent.

In some examples, the copper-containing agent can be administered in connection with an ocular-shaping device, such as an orthokeratology-style lens, for example. In this manner, the ocular-shaping device can re-shape or otherwise hold the eye in a desired or intended shape (e.g. a non-elongated shape) to remedy the elongation of a myopic eye while improving the biomechanical strength of the eye while in the desired shape. In some examples, the use of a shaping device can further improve the outcome or rate of improvement of the method of treatment.

Generally, the methods described herein can increase collagen cross-linking in the cornea as compared to an untreated eye. More specifically, the method can increase lysinonorleucine (LNL) cross-linking density, histidinyl-hydroxylysinonorleucine (HLNL) cross-linking density, or both, as well as other collagen cross-links associated with the cornea as compared to an untreated eye. Further, the methods described herein can decrease the radial strain of the cornea by at least about 10%, 25%, or 50% as compared to the cornea without treatment. Additionally, the methods described herein can decrease corneal diopter of a myopic cornea as compared to an untreated myopic cornea.

EXAMPLES

Example 1

Copper-Containing Active Agents can Increase Corneal Lysyl Oxidase Activity

Cultured corneal stroma cells from normal corneas and corneas having low corneal stiffness (n=3 each) in 10% FBS DMEM were either exposed to BSS control or 0.0016 mg/mL $CuSO_4$ in balanced salt solution (BSS) then filtered through a 0.25 µm filter. Conditioned culture medium underwent a peroxidase-coupled fluorometric activity assay for lysyl oxidase (LOX).

Tissues were collected under sterile techniques in an operative setting. Tissue samples were stored in a 10 cm tissue culture dish in an Optisol solution. Corneal tissue was suspended in 15% fetal bovine serum (FBS) DMEM/F12 with penicillin/streptomycin. Epithelium and Descemet's membrane were removed mechanically under a stereo microscope. The samples were further cut into small pieces by a surgical scissor, and added to 1 mg/mL collagenase; 10 mL per cornea was used. The sample pieces were plated to a 10 cm tissue culture dish and placed in a tissue culture incubator at 37° C. with 5% $CO_2$. After 5 days, the cells were harvested and plated in 10% FBS DMEM without phenol red.

LOX enzyme activity in culture medium was measured using a peroxidase-coupled fluorometric assay using Amplex red. Briefly, the corneal stroma cells were plated to 6 well plate at $0.2 \times 10^{\wedge}6$ cells with 2 mL culture medium. After 3 days, the culture was harvested for LOX enzyme activity assay. 50 µL of each culture medium was placed in a black 96 well plate. Then, 50 µL of 2× assay buffer (2.4 M urea, 100 mM sodium borate (pH 8.2), 20 mM 1,5-diaminopentane, 20 µM Amplex red and 2 unit/mL Horseradish peroxidase). As a parallel assay, 500 µM aminopropionitrile (BAPN) was added, which can diminish LOX activity completely. The fluorescence of oxidized Amplex red was recorded every 10 minutes using fluorescence plate reader. After subtracting the background fluorescence, the fluorescence intensity was plotted against the incubation time (FIGS. 1A and 1B).

Figure 1B:
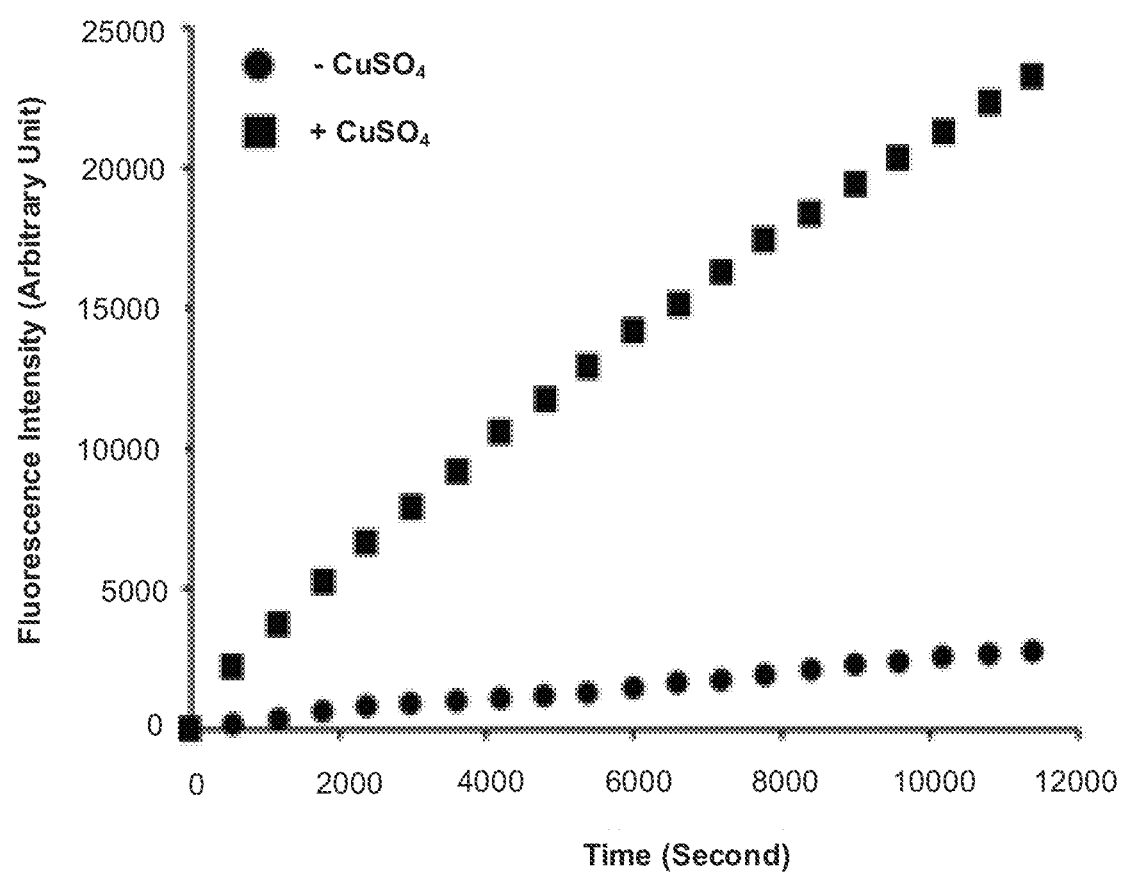
FIG. 1B is another graph showing increased lysyl oxidase activity in corneal fibroblast cells in response to Cu treatment.

Based on the peroxidase-coupled fluorometric lox activity assay, and as illustrated in FIGS. 1A-1B, it can be seen that copper dramatically increased LOX enzyme activity in fibroblast cells from normal corneas and corneas having low corneal stiffness. This indicated that copper has the potential to increase collagen cross-linking by enhancing LOX activity in myopic corneas.

Example 2

Treatment with a Copper-Containing Agent Increases Corneal Strength

Cornea radial strain measurements were performed on human cadaver corneas and on rabbit corneas. Human cadaver corneas (n=2 pairs) were cultured as previously mentioned in Example 1. The treated group was immersed in 0.0016 mg/ml $CuSO_4$ for 2 weeks. The samples also contained a small portion of sclera at both ends. Mineral oil was applied on the surface of the sclera-cornea-sclera strip to minimize tissue dehydration. Rabbit corneas were divided into 4 groups. Two groups were treatment groups receiving either $CuSO_4$ pentahydrate 0.0025 mg/ml three times per day or $CuSO_4$ pentahydrate 0.0025 mg/ml once per day. Two groups served as control receiving only BSS.

The sample was coupled between a motor and a transducer that applied a controlled pressure from 5-30 mmHg and measured the resultant radial strain. The sample length between the two gripping jaws was approximately 10 mm. Sample geometric information, including width and thickness, was input into the Rheometrics System Analyzer (RSA) control panel. Sample thickness was measured by an ultrasound pachymeter (DGH 550 Pa-chette2; DGH Technology, Exton, Pa.).

Figure 2:
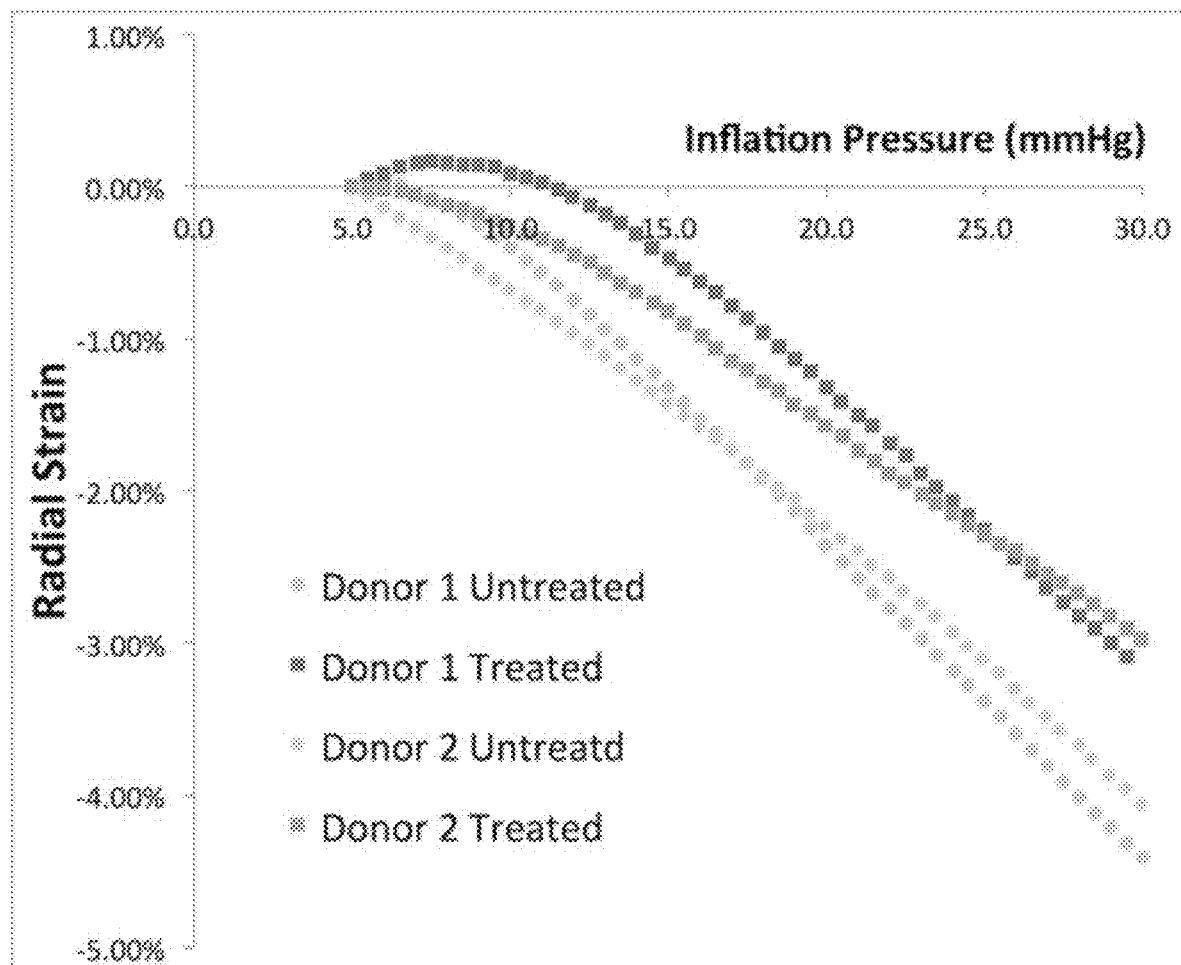
FIG. 2 is a graph showing increased corneal strength in response to Cu treatment.
Figure 3:
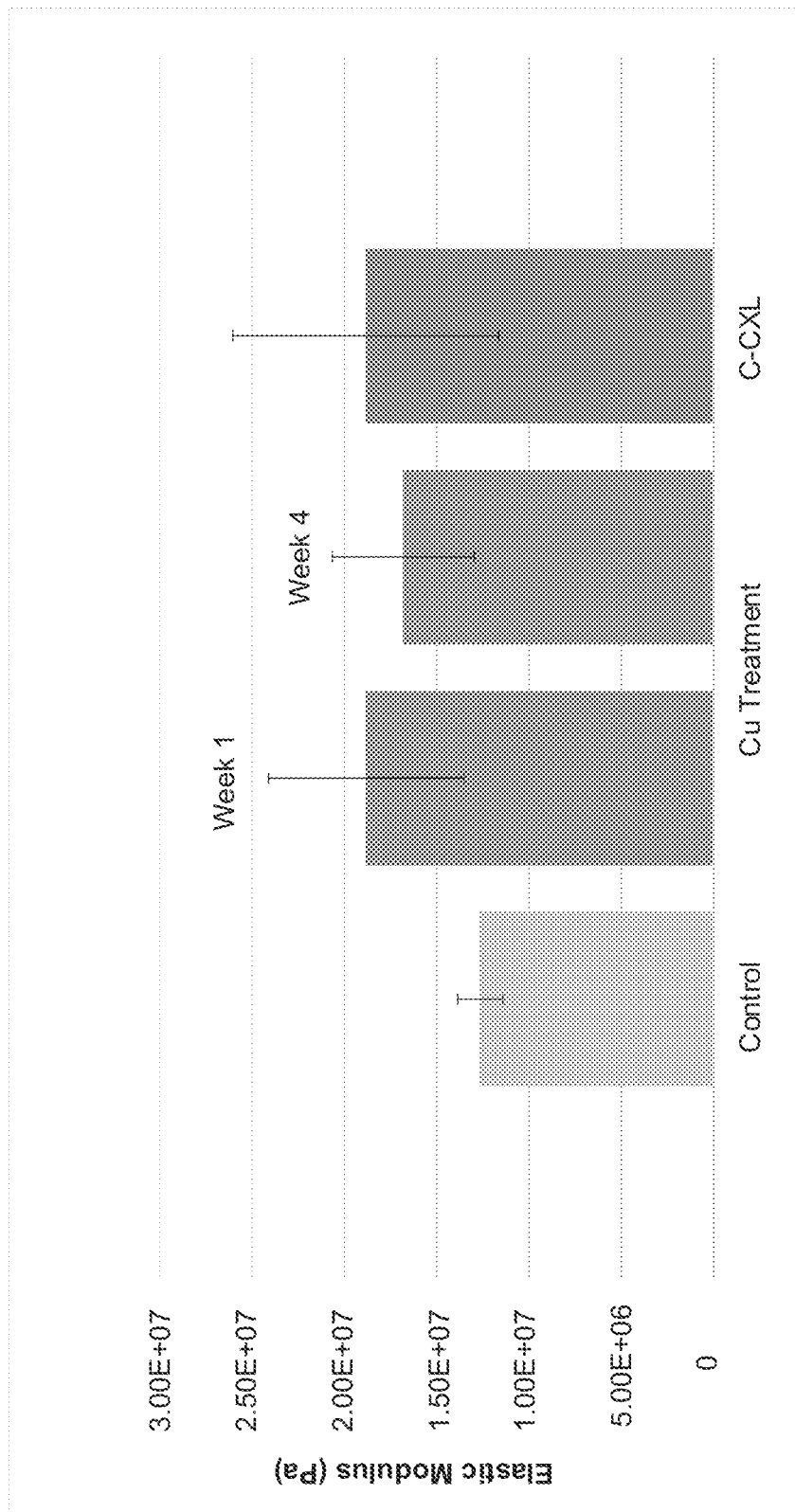
FIG. 3 is a chart showing improved corneal biomechanics in response to Cu treatment.

The results show a marked increase in stiffness and decrease in radial strain after copper sulfate treatment (FIG. 2). The average peak radial strain induced by ocular pulse at 20 mmHg in treated corneas was about 1.5 times lower than that in untreated corneas. This represents about a 50% increase in corneal strength, demonstrating that cross-linking results in a stiffer corneal response. Further, as illustrated in FIG. 3, treatment with $CuSO_4$ pentahydrate also provided corneal biomechanics comparable to that seen with laser cross-linking.

Example 3

Rabbit Corneal Topography

Corneal curvature of specific areas was monitored by corneal topography, which displays results in dioptric values. Copper sulfate pentahydrate ($CuSO_4$) at 0.0025 mg/ml was administered to New Zealand white rabbits at a dose of once per day and three times per day. Additionally, a high concentration sample of 0.025 mg/ml $CuSO_4$ pentahydrate was administered to New Zealand with rabbits once per day during the treatment period. Three different controls were administered either no drops, BSS, or artificial tears. Each of the 6 groups included 6 test subjects each. Topography images were taken before treatment and weekly for 5 weeks. Diopter measurements were the mean K values and at 3 mm. These values were compared to diopter measurements in laser cross-linked corneas after 1 month and 1 year.

Figure 4:
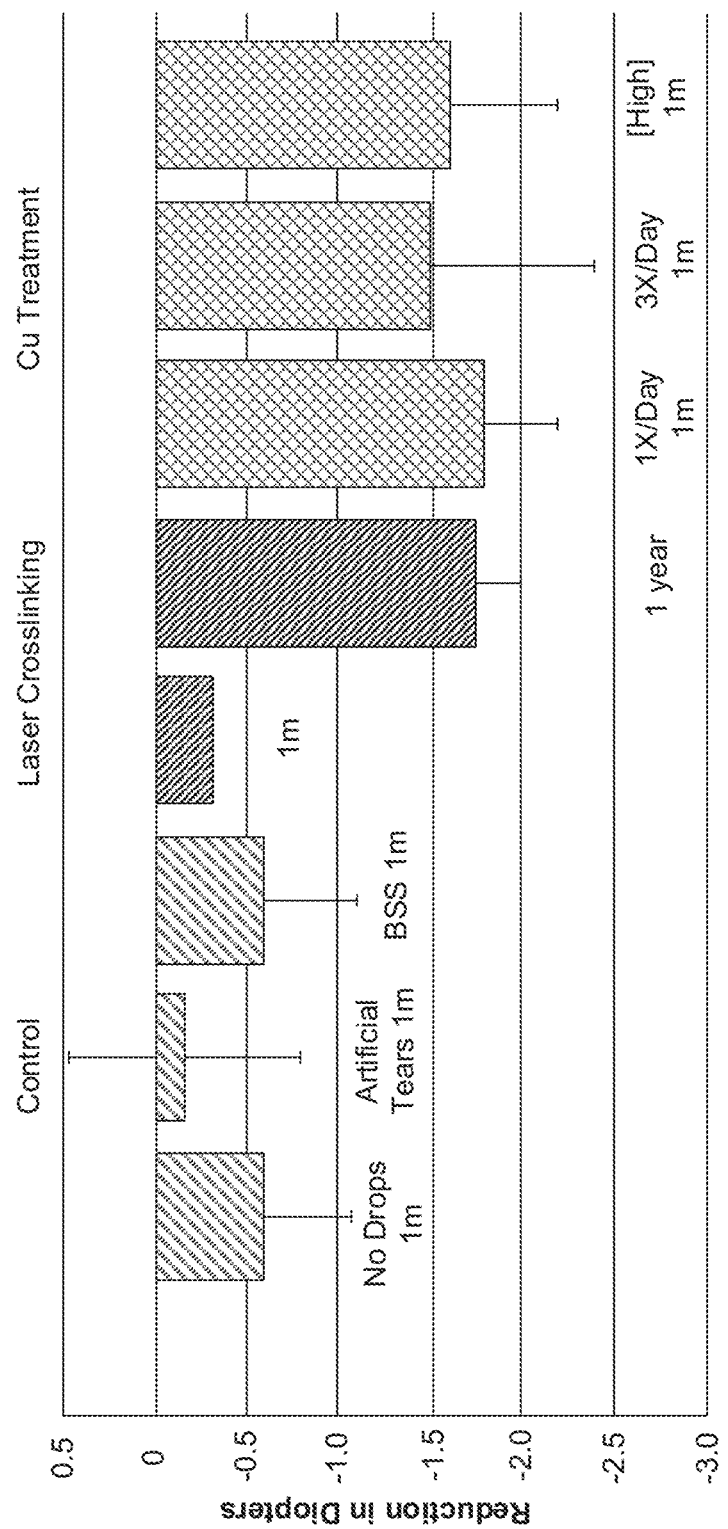
FIG. 4 is a chart showing decreased corneal diopter measurements in response to Cu treatment.

As can be seen in FIG. 4, there was a greater decrease in diopter measurements in the treatment groups as compared to the control groups. Further, 1 month of treatment with $CuSO_4$ provided similar diopter measurements as those observed in laser cross-linked corneas after 1 year.

Example 4

Safety of Copper Eye Drops In Vivo

Copper sulfate ($CuSO_4$) pentahydrate solution was prepared at a concentration of 0.0025 mg/ml and administered three times a day (TID) or once a day (QD) to rabbits. An anterior segment evaluation was performed with slit-lamp biomicroscopy and Heidelberg Spectralis anterior segment optical coherence tomography (AS-OCT). Two rabbits (n=4 eyes) were sacrificed at each of day 1, week 1, week 4, and week 6 for copper levels in eye tissues and compared to control (no drops) rabbits. Aqueous humor, vitreous, retina, cornea, lens, and blood samples were analyzed for copper ions using inductively coupled plasma mass spectrometry (ICP-MS).

Rabbits (n=2) were sacrificed after 42 days by intravenous injection of 0.3 ml/kg euthanasia solution and the eyes were enucleated for histological evaluations and reading for signs of inflammation, tissue damage, scarring and fibrosis. The anterior section of the eyes were fixed in 10% formaldehyde-glutaraldehyde solution, dehydrated in a graded series of alcohol, embedded in paraffin, and sectioned with a microtome. The sections were stained with appropriate staining (hematoxylin and eosin and Masson Trichrome).

Figure 5A:
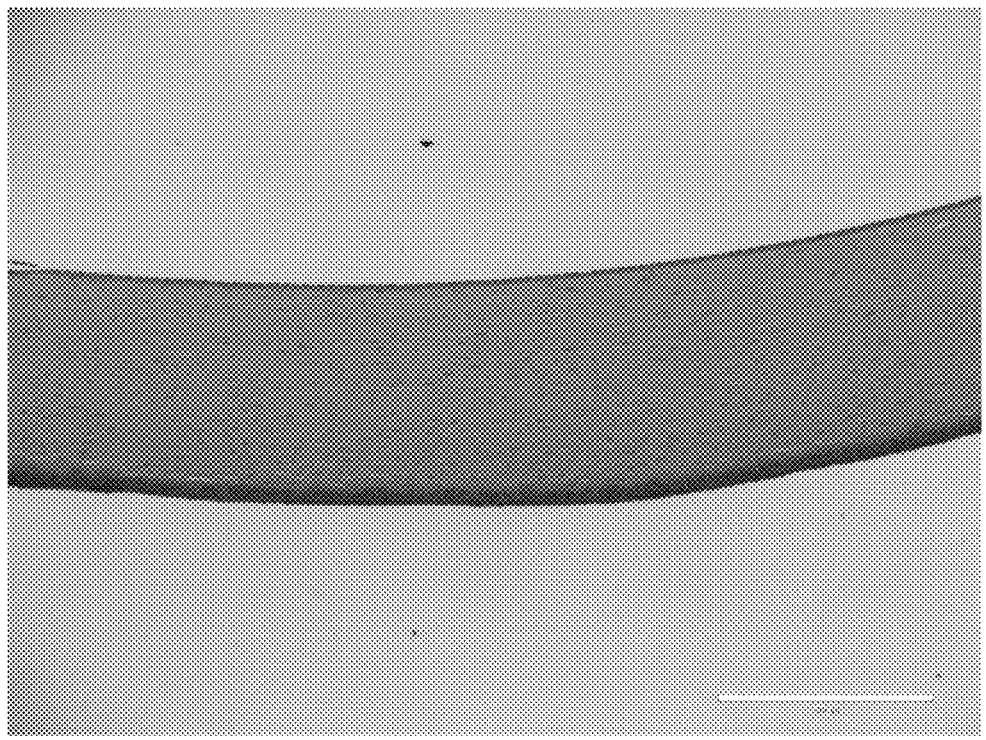
FIG. 5A illustrates an image of a stained cornea after 6 weeks of Cu treatment.
Figure 5B:
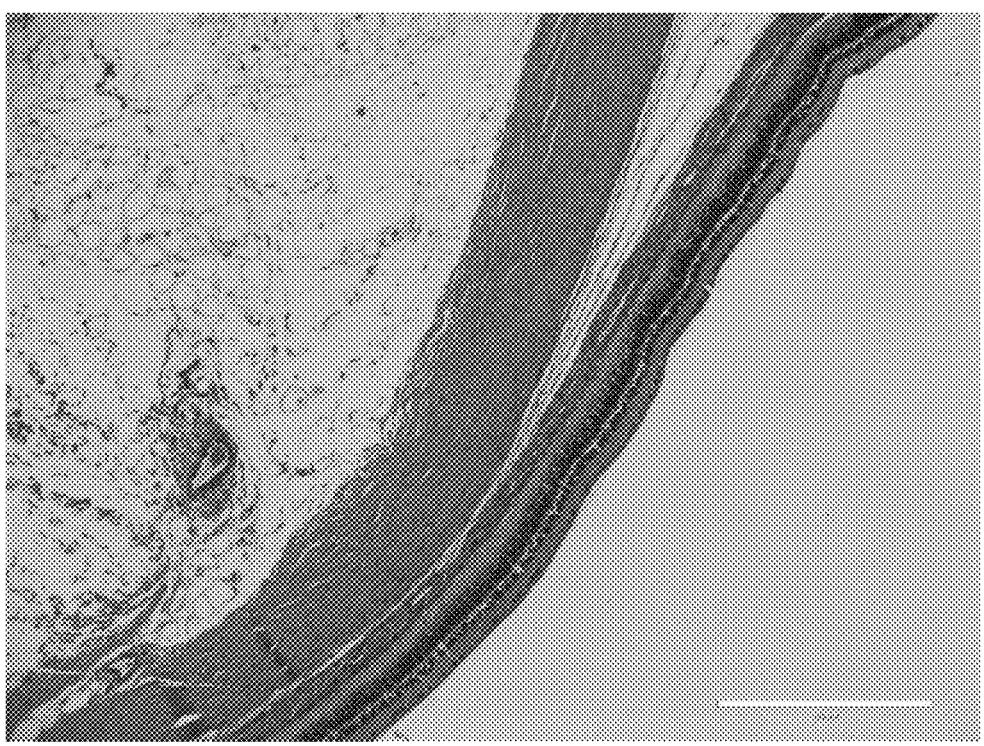
FIG. 5B illustrates an image of a stained retina/choroid after 6 weeks of Cu treatment.

There was no effect on electroretinography (ERG) measurements due to treatment with Cu. Further, there was no observed toxicity in any of the dissected eye tissues. Additionally, there was no observed corneal haze, whereas the laser cross-linking can induce corneal haze for up to about 1 year. These results are further illustrated in FIGS. 5A-5B. FIG. 5A illustrates images of a hematoxylin and eosin stained cornea after 6 weeks of Cu treatment. FIG. 5B illustrates images of a hematoxylin and eosin stained retina/choroid after 6 weeks of Cu treatment.

Example 5

Copper Treatment Induces Central Corneal Flattening in Healthy Rabbit Corneas In Vivo New Zealand white rabbit right eyes (n=3) were treated with 0.0016 mg/ml $CuSO_4$ 3×/day for 24 days. Left eyes were treated with BSS (TID) for 24 days and served as controls. Corneal-OCT pictures were taken at baseline and at day 24.

Figure 6A:
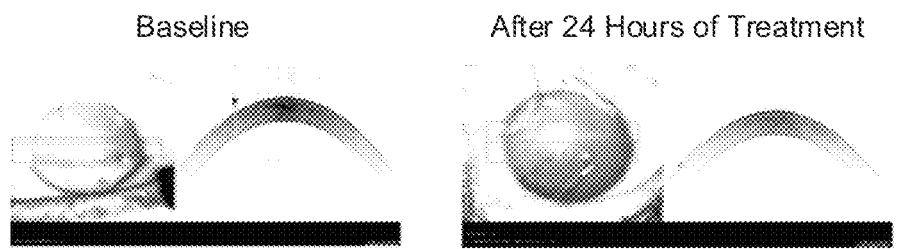
FIGS. 6A-6F present OCT images before and after BSS and $CuSO_4$ treatment. Control eyes FIGS. 6A, 6B, and 6C received BSS treatment. Treatment eyes FIGS. 6D, 6E, and 6F received $CuSO_4$ treatment.
Figure 6B:
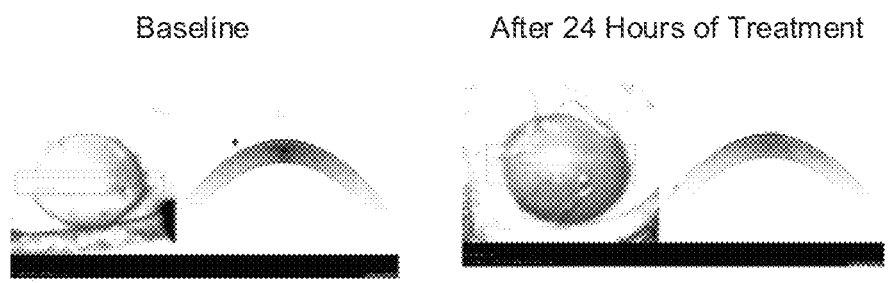
Figure 6C:
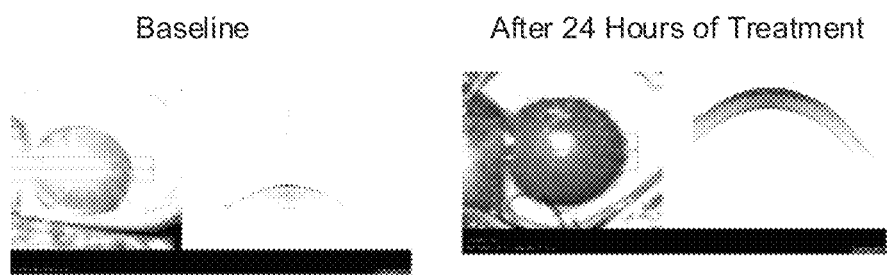
Figure 6D:
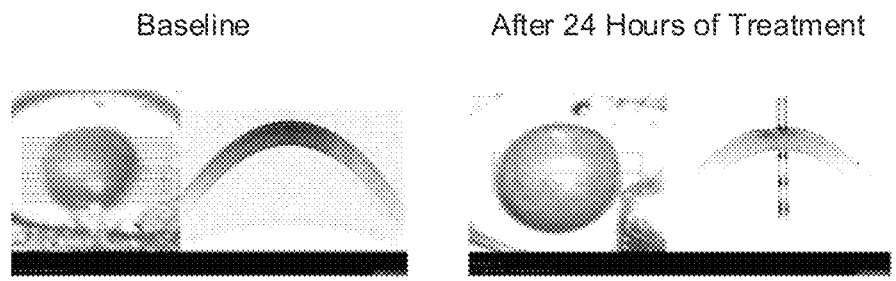
Figure 6E:
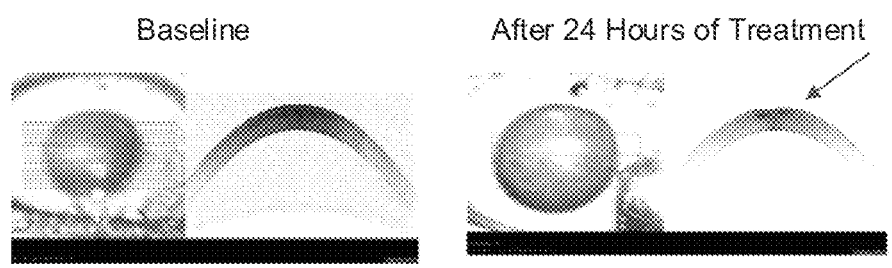
Figure 6F:
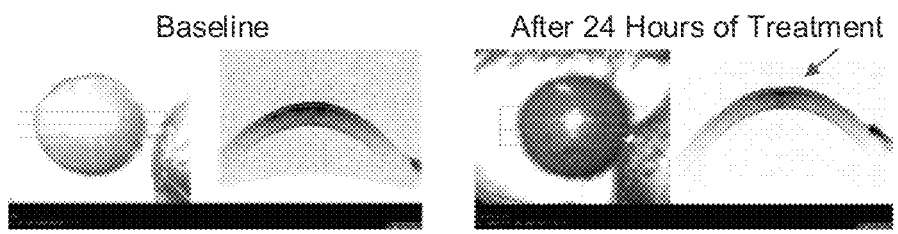

As illustrated in FIGS. 6A-6F, the representative OCT pictures show reproducible results where the central part of the right eye corneas (treated with $CuSO_4$) showed cornea flattening in all 3 treatment eyes FIGS. 6D, 6E, and 6F (see arrows) compared to the control eyes FIGS. 6A, 6B, and 6C. This is due to increase in cross linking activity. In addition, as shown in the OCT, the cornea epithelial layer is intact suggesting there was no gross toxicity to the corneas. Slit-lamp examination revealed no inflammation or opacification.

Example 6

Copper Treatment Slows Progression of Spontaneous Myopia in Albino Guinea Pigs

Figure 7A:
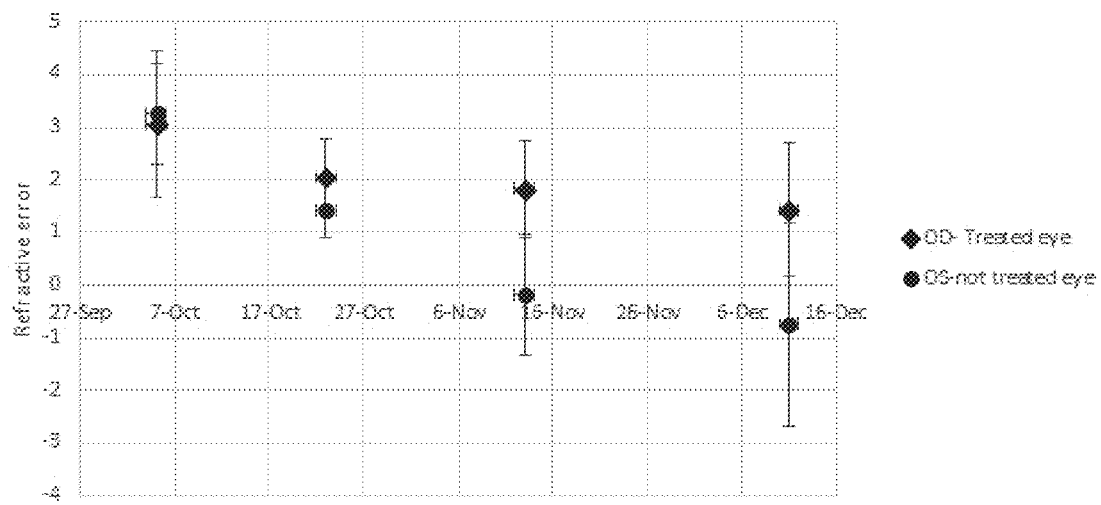
FIG. 7A is a graph (with error bars) of average refractive error for treatment eyes (OD) and non-treatment eyes (OS) in albino guinea pigs during a 6 week treatment regimen with $CuSO_4$ pentahydrate.
Figure 7B:
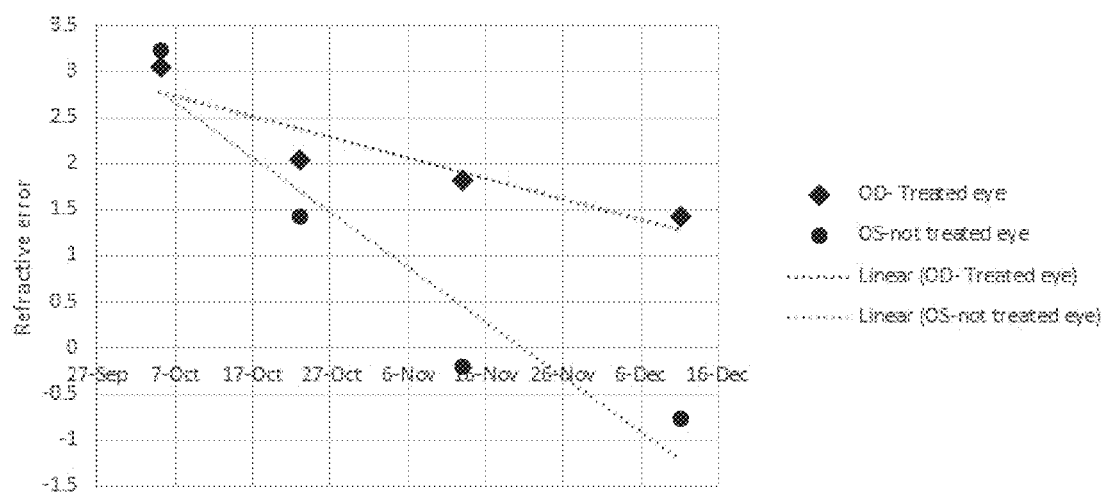
FIG. 7B is a graph (with linear fit) of average refractive error for treatment eyes (OD) and non-treatment eyes (OS) in albino guinea pigs during a 6 week treatment regimen with $CuSO_4$ pentahydrate.

Progressive myopia occurs more often in albino guinea pigs than in their wild type counterparts, even without imposing diffusers or lenses. Guinea pigs were subjected to a cycle of 12 hours of light/12 hours of dark. An eye drop including 0.0025 mg/ml $CuSO_4$ pentahydrate in phosphate buffered ophthalmic solution was administered at approximately 2 weeks of age to the right eyes (OD) of albino guinea pigs (n=4). Left eyes (OS) received control drops (ophthalmic vehicle only). Eye drops (approximately 30 µL) were administered 3 times per day for approximately 6 weeks. Refractive error was measured by a pediatric ophthalmologist prior to treatment on day 1 and at subsequent timepoints according to the schedule depicted in FIGS. 7A-7B. In further detail, refractive error was measured by streak retinoscopy in hand-held, awake animals in which cyloplegia had been previously induced with approximately 2 drops of 1% cyclopentolate. Stable refractive errors were generally obtained after 15 minutes and when there was no pupil response. FIGS. 7A-7B present average refractive error measurements for the test subjects in each eye with error bars and linear fit, respectively. As can be seen from FIGS. 7A-7B, copper treatment was effective in reducing myopic progression in the treatment eye. It is further noted that histopathological analysis demonstrated no observed toxicity in dissected eyes and IOP measurements were within normal limits of 15-25 mmHg for all eyes during the study (data not shown).

Example 7

Increase in Lysinonorleucine (LNL) Crosslinks in Treated Eyes

Figure 8:
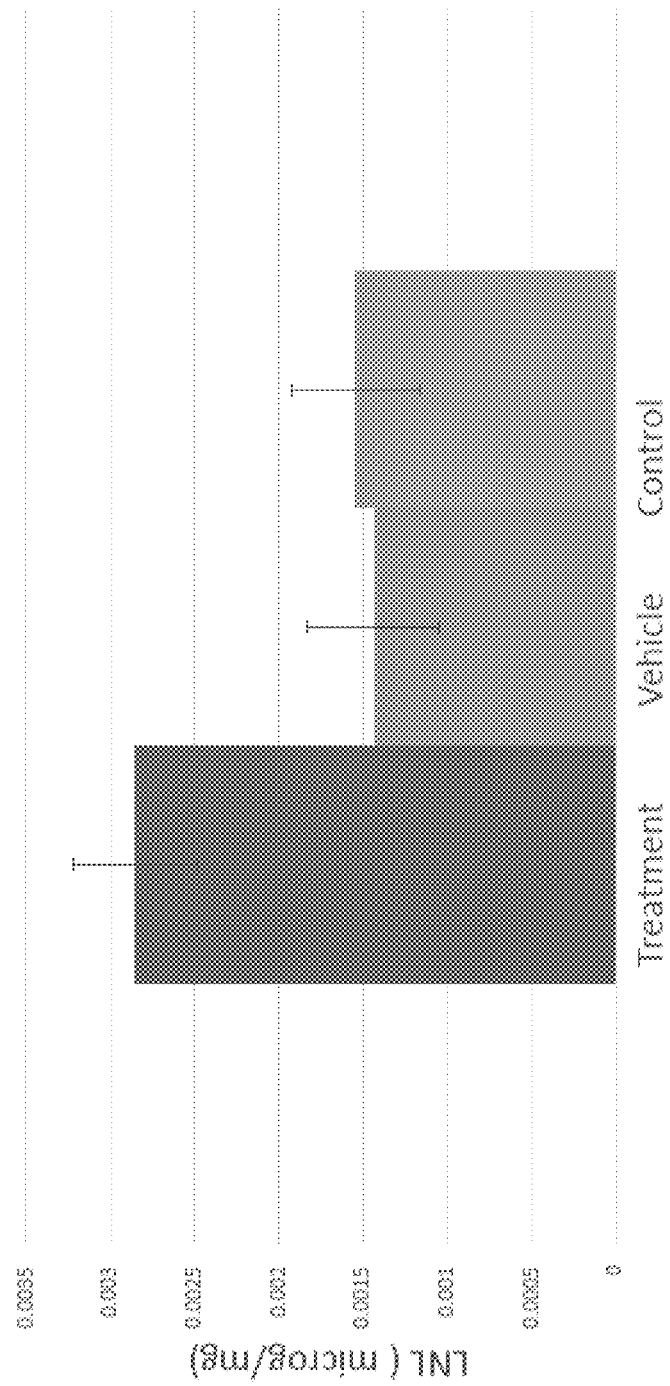
FIG. 8 is a graph of LNL concentration in treatment eyes ($CuSO_4$ pentahydrate), vehicle eyes, and control eyes of rabbits after a 6 week treatment regimen.

New Zealand white rabbit right eyes were separated (n=6 per group) into treatment group (0.0025 mg/ml $CuSO_4$ pentahydrate in phosphate buffered ophthalmic solution), vehicle group (phosphate buffered ophthalmic solution), and control group (no drops). Drops were administered 3 times per day for 6 weeks in treatment eyes. Animals were followed weekly for TOP measurements, topography and ocular response analyzer. At the end of the 6 weeks, rabbits were sacrificed and eye was immediately dissected within 30 minutes of sacrifice. Recovered corneas weight was recorded. Samples were reduced with $NaBH_4$ at room temperature then washed with water twice, dried, and hydrolyzed with 6N HCl in vacuo for 18 hours at 110° C. Post hydrolysis, cross-link enrichment was carried out by using a cellulose mini-column method. LNL was measured by mass spectroscopy. As can be seen in FIG. 8, LNL crosslinking increased in treated corneas compared to the vehicle and control groups. This indicates a stiffening of the cornea in the treatment group relative to the vehicle group and the control group.

It should be understood that the above-described methods are only illustrative of some embodiments of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that variations including, may be made without departing from the principles and concepts set forth herein.

What is claimed is:

1. A method of treating or preventing progression of myopia, comprising:
    administering a therapeutically effective amount of an ophthalmic composition to an eye of a subject during a treatment period, said ophthalmic composition comprising:
        an amount of a copper-containing agent that is sufficient to increase corneal lysyl oxidase activity in an eye of a subject in an amount sufficient to treat myopic progression, wherein the amount of copper present in the composition is from about 0.02 mg/ml to about 1 mg/ml, and
        a pharmaceutically acceptable carrier.
2. The method of claim 1, wherein the ophthalmic composition is formulated as one of a solution, a suspension, an emulsion, a gel, a hydrogel, a thermo-responsive gel, a depot, a film, a gellating suspension, a contact lens, or a punctal plug.
3. The method of claim 1, wherein the ophthalmic composition is formulated as a sustained release composition that is configured to release the copper-containing agent over a period of from about 2 days to about 6 months.
4. The method of claim 3, wherein administration is performed via one or more of placement of the composition in a cul-de-sac of the eye, placement of the composition in a conjunctival fornix of the eye, and placement of the composition in a sub-tenon's space of the eye.
5. The method of claim 3, wherein the ophthalmic composition is configured to deliver from about 0.0001 μg to about 5500 μg of copper per day to the eye of the subject, on average.
6. The method of claim 1, wherein the copper-containing agent is present in the composition in an amount from about 0.002 wt % to about 15 wt %.
7. The method of claim 1, wherein the copper-containing agent is a member selected from the group consisting of copper sulfate, copper carbonate, copper acetate, copper chloride, copper hydroxide, copper gluconate, copper bromide, copper fluoride, copper nitrate, copper iodide, copper perchlorate, copper molybdate, copper thiocyanate, copper tartrate, copper tetrafluoroborates, copper selenide, copper pyrophosphate, GHK-copper, tetra-amine copper sulfate, copper-histidine, copper-glycinate, and combinations thereof.
8. The method of claim 1, wherein the pharmaceutically acceptable carrier includes at least one of a tonicity agent, a solubilizing agent, a thickener, a polymer, a buffer, a preservative, a pH adjuster, and water.
9. The method of claim 1, wherein the composition has a tonicity of from about 200 mOsm/kg to about 600 mOsm/kg.
10. The method of claim 1, wherein the composition has a pH of from about 5.5 to about 8.5.
11. The method of claim 1, wherein the composition further comprises an additional active ingredient.
12. The method of claim 11, wherein the additional active ingredient is a member selected from the group consisting of riboflavin, rose bengal, hydroxylysine, a calcium-containing agent, a magnesium-containing agent, a silver-containing agent, an aluminum-containing agent, a zinc-containing agent, iron-containing agent, acai extract, decorin, biglycan, keratocan, lumican, mimican, fibromodulin, type VI collagen, type X collagen, type XII collagen, type XIV collagen, atropine, homatropine, cyclopentolate, pirenzepine, 7-methylxanthanine, and combinations thereof.
13. The method of claim 11, where the additional active ingredient is included in the composition in an amount from about 0.001 wt % to about 0.1 wt %.
14. The method of claim 1, wherein the ophthalmic composition is formulated as an eye drop and carried in a container adapted to dispense the composition in a dropwise manner at a drop volume of from about 5 μl to about 100 μl.
15. The method of claim 1, wherein the composition is administered at from 1 to 4 time points per day per eye in need thereof.
16. The method of claim 15, wherein from about 5 μl to about 100 μl of the composition is administered at each time point.
17. The method of claim 1, wherein the composition is administered in connection with an ocular-shaping device configured to re-shape an elongated myopic eye.
18. The method of claim 1, wherein the subject is a human subject having an age of about 3 years to about 25 years.

19. The method of claim 1, wherein the treatment period is from about 6 months to about 5 years.

\* \* \* \* \*